United States Patent
Keegan et al.

(10) Patent No.: US 9,662,201 B2
(45) Date of Patent: May 30, 2017

(54) DRUG-ELUTING STAPES PROSTHESIS

(71) Applicants: Massachusetts Eye and Ear Infirmary, Boston, MA (US); The Charles Stark Draper Laboratory, Inc., Cambridge, MA (US)

(72) Inventors: Mark E. Keegan, Littleton, MA (US); Michael J. McKenna, Southborough, MA (US)

(73) Assignees: Massachusetts Eye and Ear Infirmary, Boston, MA (US); The Charles Stark Draper Laboratory, Inc., Cambridge, MA (US)

( * ) Notice: Subject to any disclaimer, the term of this patent is extended or adjusted under 35 U.S.C. 154(b) by 0 days.

(21) Appl. No.: 14/801,649

(22) Filed: Jul. 16, 2015

(65) Prior Publication Data
US 2015/0320551 A1 Nov. 12, 2015

Related U.S. Application Data

(62) Division of application No. 12/164,861, filed on Jun. 30, 2008, now abandoned.

(60) Provisional application No. 60/947,821, filed on Jul. 3, 2007.

(51) Int. Cl.
*A61F 2/18* (2006.01)
*A61L 27/54* (2006.01)

(52) U.S. Cl.
CPC ............... *A61F 2/18* (2013.01); *A61L 27/54* (2013.01); *A61F 2002/183* (2013.01); *A61F 2230/0004* (2013.01); *A61F 2230/0069* (2013.01); *A61F 2240/001* (2013.01); *A61F 2250/0067* (2013.01); *A61L 2300/602* (2013.01); *Y10T 29/49826* (2015.01); *Y10T 29/49828* (2015.01)

(58) Field of Classification Search
CPC ....... A61F 2/18; A61F 2002/183; A61L 27/54
See application file for complete search history.

(56) References Cited

U.S. PATENT DOCUMENTS

| | | | |
|---|---|---|---|
| 3,711,869 A * | 1/1973 | Shea, Jr. | A61F 2/18 623/10 |
| 3,899,822 A | 8/1975 | Armstrong | |
| 4,052,754 A | 10/1977 | Hornsy | |
| 5,171,240 A * | 12/1992 | Hanwong | A61F 2/18 606/1 |
| 5,433,749 A * | 7/1995 | Clifford | A61F 2/18 600/25 |

(Continued)

FOREIGN PATENT DOCUMENTS

| | | |
|---|---|---|
| DE | 202005005515 | 6/2005 |
| WO | 2007/038949 | 4/2007 |
| WO | 2008/014234 | 1/2008 |

OTHER PUBLICATIONS

International Search Report and Written Opinion for Application No. PCT/US08/068763 dated Oct. 19, 2009 (15 pages).

(Continued)

*Primary Examiner* — Bruce E Snow
*Assistant Examiner* — Melissa Hoban
(74) *Attorney, Agent, or Firm* — Fish & Richardson P.C.

(57) ABSTRACT

A medical implant device includes a prosthesis adapted to replace at least a portion of a bone. The prosthesis includes a drug-eluting polymer adapted to deliver a drug to at least a portion of an area surrounding the prosthesis.

19 Claims, 3 Drawing Sheets

(56) References Cited

U.S. PATENT DOCUMENTS

| | | |
|---|---|---|
| 6,197,060 B1 | 3/2001 | Knox |
| 6,537,199 B1 * | 3/2003 | Muller et al. |
| 6,554,861 B2 * | 4/2003 | Knox .................... A61F 2/18 |
| | | 600/25 |
| 6,685,697 B1 | 2/2004 | Arenberg et al. |
| 6,726,719 B2 | 4/2004 | Antonelli et al. |
| 7,087,081 B2 * | 8/2006 | Prescott ................ A61F 2/18 |
| | | 623/10 |
| 7,163,557 B2 | 1/2007 | D'Eredita et al. |
| 7,192,445 B2 | 3/2007 | Ellingsen et al. |
| 2001/0037151 A1 | 11/2001 | Knox et al. |
| 2002/0062699 A1 | 5/2002 | Kimura |
| 2003/0097178 A1 | 5/2003 | Robersson et al. |
| 2003/0130734 A1 | 7/2003 | Antonelli et al. |
| 2003/0220700 A1 | 11/2003 | Hammer et al. |
| 2003/0229333 A1 | 12/2003 | Ashton et al. |
| 2004/0022853 A1 | 2/2004 | Ashton et al. |
| 2004/0083006 A1 | 4/2004 | Ellingsen et al. |
| 2004/0127987 A1 | 7/2004 | Evans et al. |
| 2004/0133099 A1 | 7/2004 | Dyer et al. |
| 2005/0143808 A1 | 6/2005 | Hossainy et al. |
| 2006/0067982 A1 | 3/2006 | Haapakumpu et al. |
| 2007/0077346 A1 | 4/2007 | Ellingsen et al. |
| 2007/0255405 A1 | 11/2007 | Reitan et al. |
| 2008/0086113 A1 | 4/2008 | Tenney et al. |
| 2008/0097603 A1 | 4/2008 | Brosnahan et al. |

OTHER PUBLICATIONS

Treace H.T., "Biomaterials in Ossiculoplasty and History of Development of Prostheses for Ossiculoplasty," Otolaryngologic Clinics of North America, 27(4):655-662 (1994).

* cited by examiner

FIG. 1A    FIG. 1B    FIG. 1C
         PRIOR ART
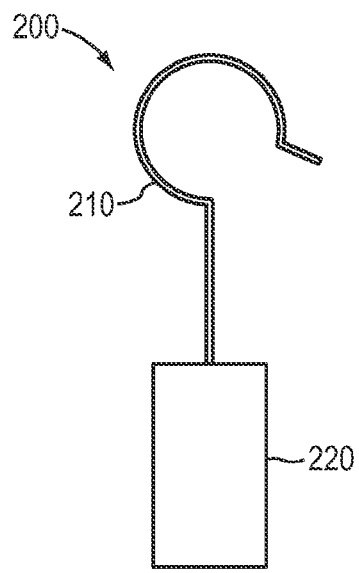
FIG. 2
PRIOR ART

DRUG-ELUTING STAPES PROSTHESIS

CROSS-REFERENCE TO RELATED APPLICATION

This application is a divisional of U.S. patent application Ser. No. 12/164,861, filed on Jun. 30, 2008, which claims priority to and the benefit of U.S. provisional patent Application No. 60/947,821, filed on Jul. 3, 2007, the disclosures of which are incorporated herein by reference in their entirety.

TECHNICAL FIELD

In various embodiments, the invention relates to devices and techniques for use in the surgical treatment of the middle ear. More particularly, described herein are embodiments of a drug-eluting stapes prosthesis, and associated methods of use, for relieving impaired conductive hearing of the middle ear and/or sensorineural hearing loss in the inner ear.

BACKGROUND

The human ear includes three parts, identified generally as the outer ear, the middle ear and the inner ear. The middle ear includes three small bones. The malleus, or hammer, connects to the tympanic membrane, also known as the eardrum, of the outer ear. The malleus is in turn connected to the incus, or anvil. The incus is connected to the stapes, or stirrup. These three small bones are also commonly referred to as ossicles, or collectively as the ossicular chain. The three bones operate as a lever and piston system that amplifies the force of sound vibrations. The stapes is in turn connected to the oval window, or stapes footplate, of the inner ear. The stapes applies pressure at the stapes footplate, which is transmitted to parts of the cochlea of the inner ear.

Due to disease, trauma or congenital malformation, the ossicles of the middle ear are sometimes damaged. One common cause is otosclerosis, which may result in fixation of the stapes. This may lessen or eliminate vibration of the stapes, resulting in a conductive hearing loss. As a result of otosclerosis, and other conditions, approximately 30,000 patients in the U.S. each year undergo a stapedectomy, which is a surgical procedure involving the removal of one of the bones of the middle ear responsible for transmission of vibration from the eardrum to the cochlea. Often, this procedure involves the replacement of the stapes bone with a prosthesis.

An exemplary technique for replacing the stapes bone with a prosthesis is shown in FIGS. 1A-1C, with a corresponding stapes prosthesis shown in FIG. 2. The stapes bone 110 is typically reconstructed by creating an opening 120 into the stapes footplate 130 by removal of a portion or all of the damaged stapes 110. The stapes prosthesis 200 is then placed into the newly created opening 120. The prosthesis 200 is attached to a remaining middle ear ossicle 140, referred to as the anchoring ossicle, so that sound vibrations are transmitted from the ear drum to the stapes footplate opening.

Designs for stapes prostheses vary somewhat, but in general, as illustrated in FIG. 2, they include a thin wire 210. The thin wire 210 is fitted on one end of a piston element 220, often constructed from a plastic such as Teflon. The exposed end of the wire 210 is crimped to the incus bone, and the piston end 220 is positioned within the hole 120 created in the stapes footplate 130, within the inner ear. The prosthesis 200 effectively mimics the function of the original stapes, carrying vibrations from the incus to the cochlea.

For approximately 6-10% of patients with a stapes prosthesis, otosclerosis is a continuing problem which may lead to failure of the prosthesis and the need for additional surgery. Drug compounds, such as bisphosphonates, help to prevent this continued bone resorption, but have side effects that make site-specific delivery of the drug desirable compared to systemic delivery.

The use of polymer-loaded matrices for delivery of drug to the middle ear has been previously described. However, such devices are limited to drug delivery and, as such, a separate additional implanted device, such as a stapes prosthesis, is still required to directly relieve the problem causing the impaired hearing.

In addition, current drug delivery devices are often difficult to place within the middle ear, especially if the device is to be large enough to hold a useful amount of drug while also allowing delivery of a drug directly into the cochlea. This may limit the allowable room for placement of an additional prosthetic device, or other treatment device, within the ear.

Other methods may also be utilized for delivery of a drug to the middle ear. For example, direct injection of drugs may be possible, although this may often be undesirable as it would require repeated invasive treatments by a physician. Other devices, such as polymeric drug carriers or microfluidic pumps, may also be implanted in a patient, allowing for the delivery of a drug to either the middle or inner ear. Again, however, a separate, additional, implanted device, such as a stapes prosthesis, would still be required.

SUMMARY OF THE INVENTION

In various embodiments, the present invention relates to systems and methods for providing a drug-eluting capability directly into a stapes prosthesis, or other medical implantable device. As a result, the exemplary systems, methods, and devices described herein enable drug delivery directly to the middle and/or inner ear and, as such, may be used for treatment of problems such as, but not limited to, prevention of otosclerosis, treatment of tinnitus, prevention of cisplatin-based ototoxicity amongst cancer patients, and sensorineural hearing loss. This, in turn, allows for a single device to be used to directly relieve a condition of the ear while also providing a method of delivering a drug.

One embodiment of the invention includes adding a drug-eluting function to an existing implantable device, such as a stapes prosthesis. This results in a device capable of providing both a drug delivery function and a prosthetic function to a portion of a body, such as the middle and/or inner ear.

In one aspect, a medical implant device includes a prosthesis adapted to replace at least a portion of a bone. The prosthesis includes a drug-eluting polymer adapted to deliver a drug to at least a portion of an area surrounding the prosthesis.

The prosthesis may be a stapes prosthesis, which may include a wire portion and a piston portion. In one embodiment, the drug-eluting polymer surrounds at least one section of the wire portion. In another embodiment, the piston portion includes the drug-eluting polymer. The piston portion may include a monolithic polymer matrix having drug molecules distributed therethrough. The piston portion may include a solid exterior. The piston portion may also include a core, within the solid exterior, that includes the drug-eluting polymer. In one embodiment the piston portion includes a semi-permeable membrane, and/or an impermeable sheath.

In general, in another aspect, embodiments of the invention feature a method of treating a portion of a body. The method includes removing a damaged portion of a body and inserting a prosthesis to replace the damaged portion of the body. The prosthesis includes a drug-eluting polymer adapted to deliver a drug to at least a portion of an area surrounding the prosthesis.

In one embodiment, the damaged portion of the body includes a stapes bone. The prosthesis may therefore be a stapes prosthesis having, for example, the structure described above.

In general, in another aspect, embodiments of the invention feature a method for manufacturing a medical implant device. The method includes coupling a wire portion to a piston portion to form a prosthesis, at least one of the wire portion and the piston portion including a drug-eluting polymer adapted to deliver a drug to at least a portion of an area surrounding the prosthesis.

These and other objects, along with advantages and features of the present invention herein disclosed, will become more apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 1A is a schematic view of a typical middle ear prior to removal of a stapes bone;

FIG. 1B is a schematic view of the middle ear of FIG. 1A, after removal of the stapes bone;

FIG. 1C is a schematic view of the middle ear of FIG. 1A, after replacement of the stapes bone with an exemplary stapes prosthesis;

FIG. 2 is a schematic side view of a standard stapes prosthesis;

DESCRIPTION

In general, embodiments of the present invention relate to systems and methods for providing a stapes prosthesis, or other appropriate medical prosthesis, with a drug-eluting function.

In one embodiment, the invention includes a drug-eluting stapes prosthesis in which a portion of the stapes prosthesis, such as a piston or wire portion, is replaced with, covered with, or enhanced with a polymer formulation impregnated with a drug. This drug may then be released over time from the polymer formulation into the ear in a controlled fashion.

Figure 3:
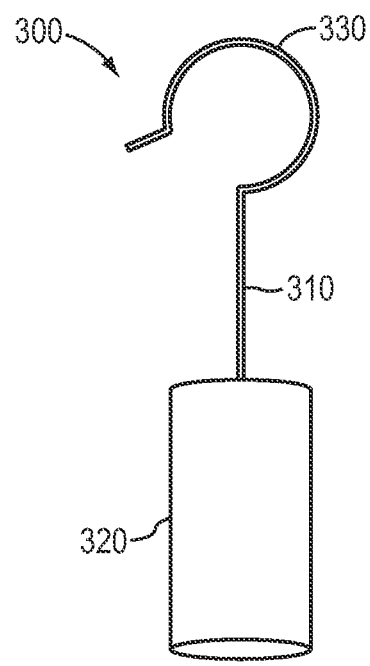
FIG. 3 is a schematic side view of a stapes prosthesis, in accordance with one embodiment of the invention.

FIG. 3 shows a stapes prosthesis 300 prior to coating a wire portion 310 thereof with a drug-eluting material. The stapes prosthesis 300 includes a piston element 320 for positioning within and/or against a stapes footplate, and the wire portion 310 for connection, for example, to the incus bone. The wire portion 310 includes a curved distal portion 330 to assist in connecting the wire portion 310 to the incus bone and crimping the wire portion 310 thereto. The piston element 320 and wire portion 310 may each be of any appropriate size and shape to allow for its positioning within an ear. For example, in one embodiment, the piston element 320 may range from 1 mm to 5 mm in length, and from 0.1 mm to 1 mm in thickness, as appropriate. In alternative embodiments, the piston element 320 may be either larger or smaller, depending upon the geometry of the ear in which the stapes prosthesis 300 is to be placed.

In one embodiment, the wire portion 310 is constructed from a metal such as titanium, nitinol, aluminum, stainless steel, or any other appropriate metal or combinations thereof. In an alternative embodiment, the wire portion 310 is constructed from a plastic, a polymeric material, or any other appropriate material. The wire portion 310 material may be selected to provide any appropriate material properties for the stapes prosthesis 300, including, but not limited to, any desired strength, flexibility, elastic and/or plastic deformability, chemical stability, sterility, and/or non-allergic property. The wire portion 310 may be attached to the piston portion 320 through an adhesive attachment, a threaded attachment, a pressure fitting, or any other appropriate attachment.

Figure 4:
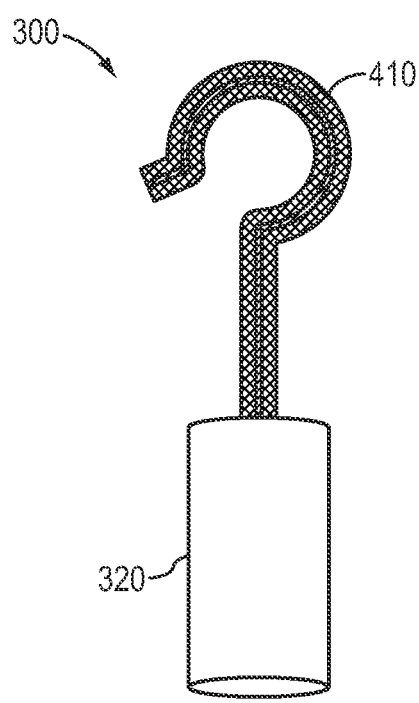
FIG. 4 is a schematic side view of a stapes prosthesis with a drug-eluting polymer coating on the wire, in accordance with one embodiment of the invention.

In one embodiment, as illustrated in FIG. 4, a drug-eluting polymer coating 410 is coated onto the wire portion 310, or a section thereof, of the stapes prosthesis 300. The drug-eluting polymer coating 410 may include, for example, drug particles dispersed within a polymer matrix such that the drug particles are released into the body at a rate and concentration based, at least in part, on the specific properties of the drug and the polymer matrix. The drug-eluting polymer coating 410 may be degradable or non-degradable, as appropriate. The polymer matrix for holding and dispersing the drug particles may include materials such as plastics, metals, organic materials, biocompatible materials, composite materials, or combinations thereof.

In an alternative embodiment, the drug-eluting polymer coating 410 may be replaced with other materials and systems for releasing a drug into the surrounding area. For example, in one embodiment, a drug may be coated directly onto the wire portion 310 as a solid, liquid, or gel. Upon placement within the ear, the drug may then dissolve, or otherwise be released from the wire portion 310, and thereby be delivered to the required location within the body. The drug may be coated to the wire portion 310 as a single layer of material, or be suspended within a degradable sterile material that dissolves within the body to release the drug. In an alternative embodiment, the wire portion 310 may be at least partially hollow, with a drug stored within. The hollow wire portion 310 may be at least partially permeable, thereby allowing the drug being stored within to be released into the surrounding area.

In other embodiments of the invention, the piston portion 320 is configured to provide drug-eluting properties in place of, or in addition to, the drug-eluting wire portion 310. This drug-eluting piston portion 320 may take a variety of forms. Exemplary embodiments are described with reference to FIGS. 5-7.

Figure 5:
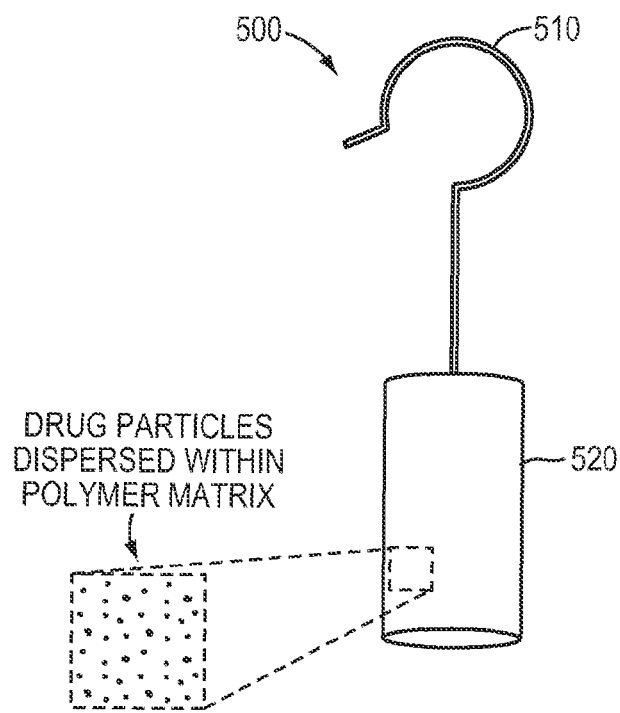
FIG. 5 is a schematic side view of a stapes prosthesis with a unitary drug-eluting polymer piston section, in accordance with one embodiment of the invention.

In one embodiment, as illustrated in FIG. 5, a stapes prosthesis 500 includes a wire portion 510 and a drug-eluting piston portion 520 that includes a single monolithic, non-degradable matrix, with drug molecules evenly distributed throughout. The wire portion 510 may include any of the materials and properties described above. The piston portion 520 is constructed from a drug-eluting polymer material including a polymer matrix configured to hold drug particles within and release the drug particles into the surrounding area at a set rate when implanted within a body. The polymer matrix may include materials such as plastics, metals, organic materials, biocompatible materials, composite materials, or combinations thereof.

In alternative embodiments, the piston portion 520 includes a plurality of sections, with one or more sections including the drug-eluting polymer material and the other sections not be loaded with the drug. The different drug-eluting polymer sections may be configured to release the same or different drugs at substantially similar or different rates, as appropriate.

Figure 6:
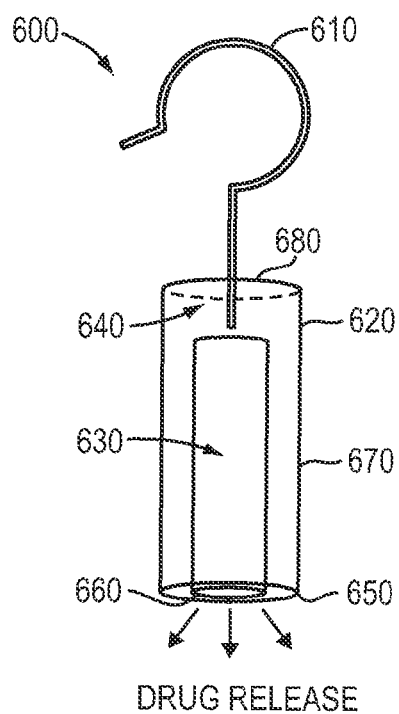
FIG. 6 is a schematic side view of a stapes prosthesis with a drug-eluting core embedded within a polymer piston section, in accordance with one embodiment of the invention.

In another embodiment, as illustrated in FIG. 6, a stapes prosthesis 600 includes a wire portion 610 and a drug-eluting piston portion 620 that includes a solid exterior 640 with a core 630. The wire portion 610 may include any of the materials and properties described above. The core 630 includes a drug-eluting material configured to hold drug particles within and release the drug particles into the surrounding area at a set rate when implanted within a body. The core 630 may include any of the materials for storing and releasing a drug described herein, such as, but not limited to, a polymer matrix, a gel, or a liquid. Example materials include, but are not limited to, degradable of non-degradable polymer matrices, hydrogels, or liquids with drugs suspended therewithin. In an alternative embodiment, the core 630 may include a hollow section configured to provide storage for a drug.

The solid outer section 640 of the piston 620 is adapted to hold the core 630 and limit the release of the drug or drugs to one or more specific directions. The solid outer section 640 may be constructed from, for example, a metal, a plastic, a ceramic, and/or a polymeric material. In one embodiment, the outer section 640 is constructed from the same material as the polymer matrix core 630. In an alternative embodiment, the outer section 640 and the polymer matrix core 630 are constructed from different materials. In one embodiment, the drug is released through a semi-permeable membrane 660 positioned against the core 630 and located at a distal end 650 of the piston portion 620. This configuration allows the drug to be released directly into the inner ear through the opening in the stapes footplate, to which the piston portion 620 is anchored, without being released into the middle ear. In an alternative embodiment, no semi-permeable membrane 660 is employed. Rather, the core 630 is exposed directly to the surroundings, at the distal end 650 of the piston portion 620.

The outer section 640 may alternatively or additionally include one or more permeable sections on its outer side wall 670, thereby allowing drug release into one or more specific areas around the outer side wall 670 of the piston portion 620. As a result, the drug can be released into the middle ear through the side wall 670 of the piston portion 620 instead of, or in addition to, being released into the inner ear through a distal end 650 of the piston portion 620. These permeable sections may include, but are not limited to, perforations and/or permeable or semi-permeable membranes. In addition, a proximal end 680 of the piston portion 620 may be configured to allow drug release.

Figure 7:
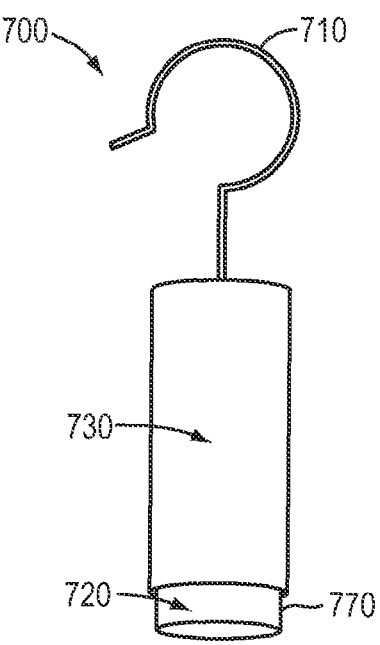
FIG. 7 is a schematic side view of a stapes prosthesis with a drug-eluting piston section embedded within an impermeable sheath, in accordance with one embodiment of the invention.

In another embodiment of the invention, as illustrated in FIG. 7, a drug-eluting piston portion 720 of a stapes prosthesis 700 includes a non-permeable coating or impermeable sheath 730 (such as a metal film) that restricts drug release from the prosthesis 700 to a selected region 770 of the piston portion 720.

In one embodiment, the impermeable sheath 730 provides an impermeable covering for at least a portion of the drug eluting piston portion 720. The impermeable sheath 730 may be moveable and may be constructed from any appropriate material including, but not limited to, a metal, a ceramic, and/or a polymer. In operation, in one embodiment, the impermeable sheath 730 is placed over a portion of the piston portion 720 to restrict the release of a drug to one section of the side wall 770 of the piston portion 720. In an alternative embodiment, the sheath 730, rather than being impermeable, may include one or more perforations, and/or permeable or semi-permeable sections, to allow a drug to be released therethrough. These perforations and/or permeable sections may be distributed over the sheath 730 in any appropriate configuration.

Other embodiments of the invention include a number of elements of the embodiments described above. For example, one embodiment of the invention includes both a drug-eluting polymer covering the wire portion of the stapes prostheses in addition to a drug-eluting piston portion. In further embodiments of the invention, any combination of elements described herein may be used to allow the prosthesis to deliver a drug, or a number of separate drugs, to targeted portions of the middle and/or inner ear. These embodiments may include wire portions adapted to deliver one or more drugs, and piston portions adapted to deliver one or more other drugs from a bottom portion of the prosthesis attached to the stapes footplate and/or out of the side and/or top of the piston.

In addition, other materials in addition to, or in place of, a drug-eluting polymer may be used in the construction of the prosthesis. These may include any appropriate biocompatible material, including, but not limited to, a metal, a plastic, a composite material, or combinations thereof.

The exemplary devices described herein feature a number of benefits over conventional stapes prostheses (such as the stapes prosthesis 200 illustrated in FIG. 2), or other medical implants. For example, combining a drug delivery system with the prosthesis device reduces the number of separate components that must be inserted into the middle ear, thereby simplifying the stapedectomy procedure and increasing patient safety. In one embodiment, the addition of the drug-eluting element to the stapes prosthesis allows for the continued treatment of otosclerosis via the drug-eluting prosthesis, without the need for any additional implants or procedures.

In addition, combining the drug-containing element with the prosthesis minimizes the diffusion distance the released drug must travel to reach the desired site of action. Although, in general, a separate drug delivery device implanted within the middle ear will be relatively close to the desired site of action, due to the limited volume of the middle ear, the closer the delivery device is placed to the desired site, the better. For example, for controlled release from small matrices, the observed drug concentration drops off rapidly as you move away from the device, such that for some applications tissues located on the order of a few millimeters from the device will not receive therapeutically useful doses of drug.

Also, for embodiments in which the drug delivery system is placed within the piston of the stapes prosthesis, the distal end of the piston may be placed in direct fluid communication with the inner ear, thereby enabling delivery of the drug directly to the inner ear, rather than relying on diffusion of the drug from the middle ear to the inner ear. This embodiment may be used, for example, in the treatment of cochlear otosclerosis, where delivery of one or more drugs directly into the cochlea, such as through the distal end of the prosthesis piston, may be of significant value. In one embodiment, drugs from the bisphosphonate class are delivered, although, in other embodiments, other appropriate drugs are delivered in place of, or in addition to, bisphosphonate class drugs.

In one embodiment, combining the drug-eluting element into the prosthesis places a limit on the payload of drug that may be carried. For example, the piston may be on the order of 2-4 mm long and 0.6 mm in diameter, thus limiting the storage space for any drug to no more than that volume. However, even given these size constraints, appropriate dosages of drug may still be encapsulated in the device to provide long-term delivery of the drug.

In one specific example, a bisphosphonate drug, such as, but not limited to, Fosamax® (i.e. Alendronate sodium), is used for the prevention of otosclerosis in the middle ear. If this drug were to be administered orally, a typical daily oral dose of approximately 10 mg would be required, with a percentage uptake of the drug from the gut in a fasted state of approximately 0.6%. This would result in an actual daily dose of approximately 60 mcg/day, and give a theoretical maximum serum concentration of approximately 12 mcg/liter or 12 ng/ml, assuming 5 liters blood volume. In contrast, an effective dose may be delivered directly to the middle ear through use of a drug-eluting stapes prosthesis, as described herein. For example, if approximately 1 cc of tissue volume is to be treated in a site-specific way, wherein the drug is delivered directly at the site of action, approximately 12 ng of drug per day is required. Using materials such as, but not limited to, poly(ethylene-co-vinyl acetate) (EVAc) as a matrix to form the piston, with only a 10% drug loading (which is considered to be a very low total percentage loading for matrices of such materials), a piston of 2 mm length and 0.6 mm diameter would contain 52.3 mcg of drug. Thus, at a requirement of 12 ng/day, the piston may be loaded with sufficient drug for 12 years of therapy (assuming the drug is substantially 100% stable within the implant, and the release rate is substantially constant over the full device lifetime).

Even assuming a less than perfect drug stability and/or linear release, the required drug therapy may be provided for many months or years using embodiments of the present invention. As such, the limited size of the exemplary devices described herein does not limit drug payload to unacceptably low levels. Rather, reasonable drug delivery rates may be provided for long periods without the need to increase the size of the prosthesis or to provide additional drug delivery systems or drug storage receptacles.

In addition to bisphosphonate delivery for the treatment and/or prevention of otosclerosis, embodiments of the invention may be used for the delivery of other drugs, and for the treatment of other conditions related to the middle and/or inner ear. In one embodiment, the drug-eluting prosthesis is used for the delivery of antioxidants. These antioxidants may, for example, be used for the protection from ototoxicity associated with the use of platinum-based chemotherapeutic agents such as cisplatin. In another embodiment, the drug-eluting prosthesis is used for the delivery of steroids, such as, but not limited to, Dexamethasone. These steroids may, for example, be used in the treatment of problems within the ear including, but not limited to, sensorineural hearing loss and Meniere's disease. In another embodiment, the drug-eluting prosthesis is used for the delivery of antibiotics, such as, but not limited to, Gentamicin. These antibiotics may, for example, be used in the treatment of problems within the ear including, but not limited to, Meniere's disease. In yet another embodiment, the drug-eluting prosthesis is used for the delivery of anti-apoptotic agents, such as, but not limited to, Caspase inhibitors. These anti-apoptotic agents may, for example, be used in the treatment of problems within the ear including, but not limited to, noise-induced hearing loss (NIHL).

Other implantable devices may also be adapted to include a drug-eluting component, allowing for targeted drug delivery to any part of the body. Devices that may utilize this drug-eluting capability include, but are not limited to, spinal implants or other bone stabilizing implants, pacemakers, insulin delivery devices or other active treatment devices, or any other appropriate device or element that is implanted into a body. The drug-eluting component of these devices may be used to deliver a drug, or multiple drugs, including, but not limited to, a painkilling or anesthetic drug, a bone growth enhancing or inhibiting drug, or other appropriate drugs for the targeted treatment of a specific portion of a body.

Having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A method of selectively administering a drug to an inner ear of a patient without administering the drug to the middle ear, the method comprising:
    removing at least a portion of a stapes bone of the patient and creating an opening in the patient's stapes footplate;
    obtaining a stapes prosthesis comprising
        (i) a wire portion adapted for anchoring to an incus bone;
        (ii) a piston portion having a proximal end coupled to the wire portion and a distal end configured to fit into the opening created in the stapes footplate, wherein the piston portion comprises a solid side wall surrounding a hollow section that opens at the distal end of the piston portion; and
        (iii) a drug-eluting core comprising a drug arranged within the hollow section, wherein the solid side wall of the piston portion is constructed to limit the release of the drug only through the distal end;
    inserting the distal end of the stapes prosthesis into the opening in the stapes footplate such that the distal end is in direct fluid communication with fluid in the inner ear; and
    connecting the wire portion of the stapes prosthesis to the incus bone;

wherein the stapes prosthesis carries vibrations from the incus bone to the inner ear and the drug-eluting core delivers the drug directly to the fluid in the inner ear through the opening into the patient's stapes footplate without releasing the drug into the middle ear.

2. The method of claim 1, wherein the piston portion comprises a drug-eluting polymer.

3. The method of claim 2, wherein the piston portion comprises a monolithic polymer matrix having drug molecules distributed therethrough surrounded by the solid side wall.

4. The method of claim 1, wherein the distal end of the piston portion comprises a semi-permeable membrane through which the drug is released to the fluid in the inner ear.

5. The method of claim 1, wherein the drug-eluting core comprises a drug-eluting material that releases the drug over time.

6. The method of claim 5, wherein the drug-eluting material comprises a polymer matrix, a gel, or a liquid that includes the drug.

7. The method of claim 6, wherein the polymer matrix comprises a non-degradable polymer matrix.

8. The method of claim 6, wherein the gel comprises a hydrogel.

9. The method of claim 1, wherein the drug comprises one or more of a bisphosphonate, antioxidant, platinum-based chemotherapeutic agent, steroid, antibiotic, and an anti-apoptotic agent.

10. The method of claim 9, wherein the drug comprises a bisphosphonate comprising alendronate sodium.

11. The method of claim 1, wherein the drug comprises one or more of dexamethasone, gentamicin, and a caspase inhibitor.

12. The method of claim 1, wherein the patient has been diagnosed with having otosclerosis or being susceptible to otosclerosis and the drug comprises a bisphosphonate.

13. The method of claim 12, wherein the bisphosphonate comprises alendronate sodium.

14. The method of claim 1, wherein the patient has been diagnosed with having Meniere's disease or being susceptible to Meniere's disease and the drug comprises one or more of a steroid and an antibiotic.

15. The method of claim 14, wherein the antibiotic comprises gentamicin.

16. The method of claim 1, wherein the patient has been diagnosed with having noise-induced hearing loss (NIHL) or being susceptible to NIHL and the drug comprises an anti-apoptotic agent.

17. The method of claim 16, wherein the anti-apoptotic agent comprises a caspase inhibitor.

18. The method of claim 1, wherein the solid side wall comprises a non-permeable coating or impermeable sheath.

19. The method of claim 18, wherein the non-permeable coating or impermeable sheath comprises a metal film.

* * * * *